US00PP27030P3

(12) United States Plant Patent
Zaiger et al.

(10) Patent No.: US PP27,030 P3
(45) Date of Patent: Aug. 9, 2016

(54) INTERSPECIFIC TREE NAMED 'FLAVOR PUNCH'

(50) Latin Name: **Interspecific *Prunus* species**
Varietal Denomination: Flavor Punch

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 95 days.

(21) Appl. No.: 14/544,254

(22) Filed: Dec. 15, 2014

(65) Prior Publication Data

US 2016/0174432 P1 Jun. 16, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Tree being a regular and productive bearer of small to medium size fruit.
3. Fruit with very good flavor and eating quality.
4. Fruit with an attractive dark red skin color.
5. Fruit with good storage and shipping qualities.

1 Drawing Sheet

Botanical designation: Interspecific *Prunus* species.
Variety denomination: 'Flavor Punch'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Sweet Pixzee 2' Interspecific (U.S. Plant Pat. No. 23,796), 'Flavor Blast' Interspecific (U.S. Plant Pat. No. 23,720), 'Autumn Treat' Interspecific (U.S. application Ser. No. 13/999,782) and the proprietary non-patented interspecific varieties '46MB665' and '162LM246'.

STATEMENT REGARDING FEDERALLY SPONSORED RESEARCH AND DEVELOPMENT

Not applicable.

ORIGIN OF THE VARIETY

The new and distinct variety of interspecific tree consists of the combination of *Prunus salicina, Prunus armeniaca, Prunus avium* and *Prunus persica*. It was originated by us in our experimental orchard located near Modesto, Calif. as a first generation cross between 'Sweet Pixzee 2' Interspecific (U.S. Plant Pat. No. 23,796) and our proprietary non-patented interspecific seedling selection with the field identification number '46MB665'. The non-patented interspecific pollen parent (46MB665) originated from crosses between our proprietary non-patented interspecific seedling selection '162LM246' and 'Autumn Treat' (U.S. Plant Pat. No. 26,192). A large number of these first generation seedlings were budded onto older established trees of 'Nemaguard' Rootstock (non-patented) to enhance earlier fruit production. Under close and careful observation the present seedling exhibited desirable fruit and tree characteristics and was selected in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree which includes [Plum×Plumcot×Cherry×Plum×Plum Peach]×[Plum×Cherry×Plum×Plumcot] is of large size, vigorous, upright growth and a regular and productive bearer of small to medium size fruit with very good flavor and eating quality. The fruit is further characterized by its firm, yellow flesh, attractive dark red skin color and good storage and shipping qualities. In comparison to its seed parent 'Sweet Pixzee 2' Interspecific (U.S. Plant Pat. No. 23,796) the fruit of the new variety is larger in size and is approximately 53 days later in maturity. In comparison to its non-patented proprietary interspecific pollen parent (46MB665) the fruit of the new variety is approximately 17 days later in maturity. In comparison to the commercial variety 'Flavor Blast' Interspecific (U.S. Plant Pat. No. 23,720) the fruit of the new variety has a darker red skin color and is approximately 7 days earlier in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies with soil type, fertility of soil and climatic conditions.

*Form*.—Upright, usually pruned to vase shape.

*Branching habit*.—Upright growth, crotch angle approximately 25°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 4 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 1000 hours at or below 45° F.

Trunk:

*Size*.—Medium. Average circumference 48.3 cm at 25.4 cm above ground on a 6 year old tree.

*Stocky*.—Medium stocky.

*Texture*.—Medium shaggy, roughness increases with age of tree.

*Color*.—Varies from 2.5Y 4/2 to 5Y 4/2.

Branches:

*Size*.—Medium. Average circumference 15.2 cm at 1.2 meters above ground. Crotch angle approximately 25°, increases with heavy fruit crop.

*Surface texture*.—New growth relatively smooth. Mature growth medium rough, roughness increases with age.

*Lenticels*.—Size — medium. Average number 47 in a 25.8 square cm section. Average length 3.9 mm. Average width 1.1 mm. Color varies from 7.5YR 6/10 to 7.5YR 5/10.

*Color*.—New growth varies from 5GY 6/8 to 10R 3/4. Mature growth varies from 10YR 2/2 to 2.5Y 2/2, varies with age of growth.

Leaves:

*Size*.—Medium. Average length 92.0 mm. Average width 37.6 mm.

*Form*.—Obovate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 16.4 mm. Average width 1.2 mm. Longitudinally grooved. Surface — glabrous. Color varies from 5GY 7/6 to 2.5YR 3/6.

*Glands*.—Type — globose. Size — small. Average length 0.8 mm. Average diameter 0.4 mm. Number varies from 2 to 5, average number 3. Located primarily on the base of leaf blade and upper portion of petiole. Color varies from 5GY 6/8 to 2.5YR 3/6.

*Stipules*.—Average number 2. Average length 6.8 mm. Edges — pectinate. Color varies from 5GY 7/8 to 5GY 6/8.

*Color*.—Upper surface varies from 7.5GY 3/4 to 7.5GY 3/6. Lower surface varies from 7.5GY 5/4 to 7.5GY 4/4. Midvein color varies from 5GY 8/6 to 5GY 7/6.

Flower buds:

*Size*.—Medium to large. Average length 10.6 mm. Average diameter 5.8 mm.

*Hardiness*.—Hardy with respect to California winters.

*Density*.—Very dense.

*Form*.—Conical, becoming elongated just before opening.

*Pedicel*.—Size — medium to large. Average length 9.5 mm. Average width 0.6 mm. Color varies from 10Y 7/8 to 2.5GY 7/8. Surface — glabrous.

*Color*.—N 9.5/ (white).

*Number of buds per spur*.—Average 11, varies from 7 to 16. Varies with age of spur.

Flowers:

*Blooming period*.—Date of First Bloom Mar. 1, 2014. Date of Petal Fall Mar. 9, 2014, varies slightly with climatic conditions.

*Size*.—Medium. Average height 11.8 mm. Average diameter 19.6 mm.

*Petals*.—Number — normally 5, alternately arranged to sepals. Size — large. Average length 11.0 mm. Average width 7.7 mm. Form — ovate. Margin — sinuate. Arrangement — semi overlapping to free. Apex — rounded. Base — truncated. Color N 9.5/(white). Both upper and lower surfaces glabrous.

*Sepals*.—Number — normally 5, alternately arranged to petals. Size — medium. Average length 3.4 mm. Average width 2.5 mm. Shape — triangular. Margin — entire. Apex — rounded to triangular. Both upper and lower surfaces glabrous. Color — upper surface varies from 5GY 6/8 to 5GY 7/8. Lower surface varies from 5R 3/10 to 2.5GY 5/6.

*Stamens*.—Average number per flower 39. Average filament length 10.1 mm. On average, the stamens are above the height of the petals. Filament color N 9.5/(white). Anther color varies from 2.5Y 7/10 to 10YR 7/12.

*Pollen*.—Self sterile, pollinator required. Color varies from 2.5Y 8/14 to 2.5Y 7/12.

*Pistil*.—Number — normally one. Surface — glabrous. Average length 9.8 mm. Position of stigma an average of 1.6 mm below anthers. Color varies from 10Y 7/8 to 2.5GY 8/8.

*Fragrance*.—Heavy.

*Color*.—N 9.5/(white).

*Pedicel*.—Average length 12.4 mm. Average width 0.7 mm. Color varies from 2.5GY 7/8 to 2.5GY 7/6. Surface — glabrous.

*Number of flowers per flower bud*.—Average 2, varies from 1 to 3.

Fruit:

*Maturity when described*.—Firm ripe and ready for consumption.

*Date of first picking*.—Aug. 16, 2014.

*Date of last picking*.—Aug. 26, 2014, varies slightly with climatic conditions.

*Size*.—Small to medium. Average diameter axially 52.5 mm. Average transversely in suture plane 53.5 mm. Average weight 102.2 grams, varies slightly with fertility of the soil, amount of thinning and climatic conditions.

*Form*.—Globose.

*Suture*.—Slightly lipped, extends from base to apex.

*Ventral surface*.—Slightly lipped.

*Apex*.—Rounded to very slightly retuse.

*Base*.—Flat.

*Stem cavity*.—Rounded to slightly elongated in suture plane. Average depth 7.5 mm. Average diameter 3.3 mm.

Stem:

*Size*.—Medium to large. Average length 16.7 mm. Average diameter 1.6 mm.

*Color*.—Varies from 10YR 5/6 to 2.5YR 3/8.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 22.5°, varies slightly with amount of fruit per tree and climatic conditions.

*Pit cavity*.—Average length 25.2 mm. Average width 16.6 mm. Average depth 5.1 mm. Color varies from 10YR 6/8 to 7.5YR 6/10.

*Color*.—Varies from 10YR 7/8 to 10YR 6/10.

Skin:

*Thickness*.—Medium.

*Surface*.—Smooth.

*Bloom*.—Moderate amount, complete coverage.

*Tendency to crack*.—None.

*Color*.—Ground color varies from 2.5Y 8.5/6 to 2.5Y 8/4. Overspread with 5R 3/8 to 5R 3/6.

*Tenacity*.—Tenacious to flesh.

*Astringency*.—Undetected.

Stone:

*Type*.—Clingstone, medium adherence.

*Size*.—Medium. Average length 24.5 mm. Average width 15.6 mm. Average thickness 9.2 mm.

*Form*.—Ovoid.

*Base*.—Flat.

*Apex*.—Pointed. Average length 1.0 mm.

*Surface*.—Slightly pitted throughout. One shallow groove on each side of suture extending from base toward apex.

*Sides*.—Unequal, one side extending further outward from suture plane.

*Ridges*.—Very narrow, small ridge near groove on each side of suture.

*Tendency to split*.—None.

*Color*.—Varies from 7.5YR 5/10 to 10YR 6/10 when dry.

Kernel:

*Size*.—Small to medium. Average length 15.8 mm. Average width 9.1 mm. Average depth 5.2 mm.

*Form*.—Ovoid.

*Viability*.—Viable, complete embryo development.

*Skin color*.—Varies from 10YR 5/8 to 7.5YR 5/8.

Use:

*Dessert*.—Market — local and long distance.

Keeping quality: Good, held firm in cold storage for 3 weeks at 38° to 42° F. without internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

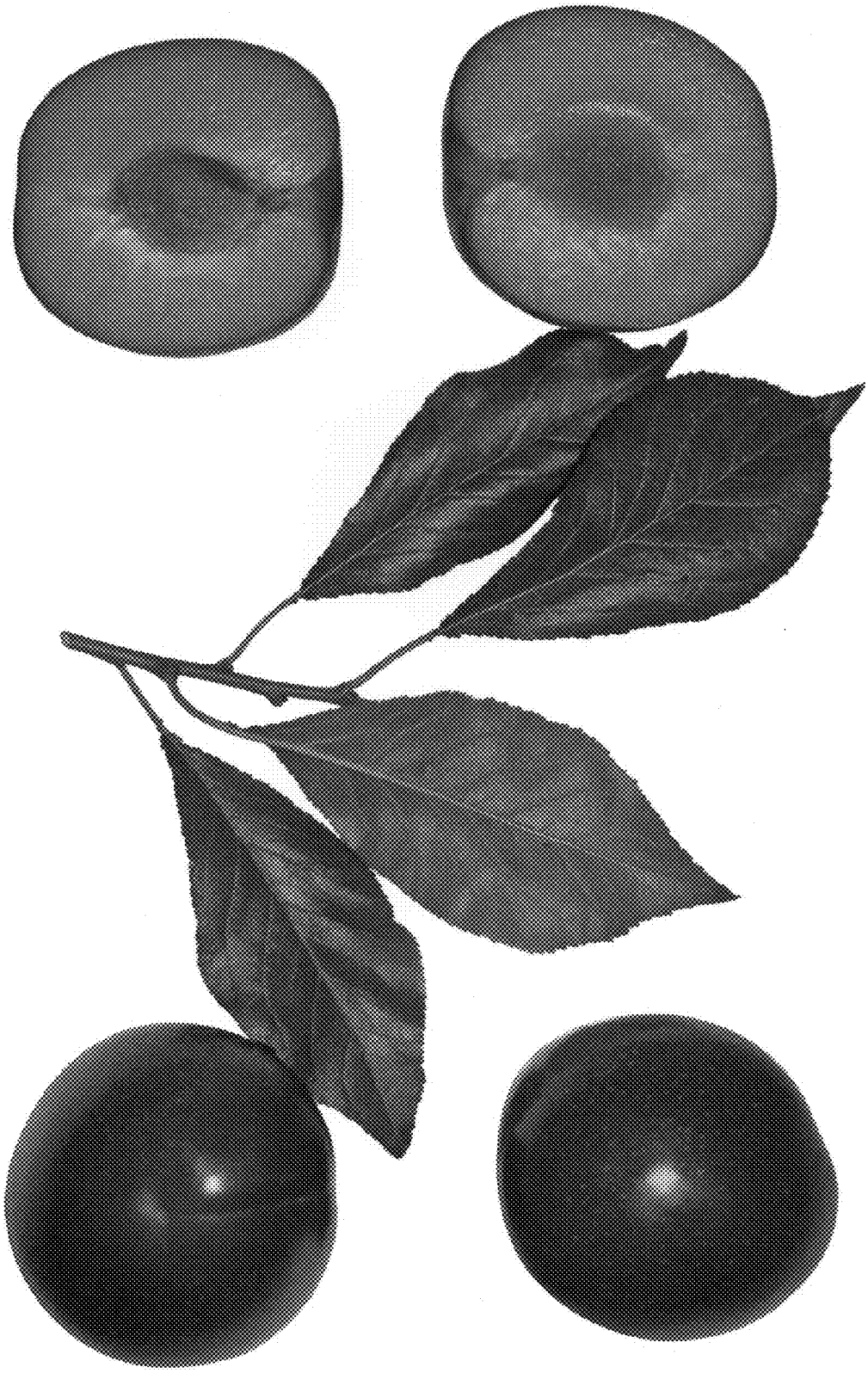

* * * * *